(12) United States Patent
Suddaby (10) Patent No.: US 8,876,845 B2
(45) Date of Patent: Nov. 4, 2014

(54) SLING BLADE TRANSECTION OF THE TRANSVERSE CARPAL LIGAMENT

(76) Inventor: Loubert Suddaby, Orchard Park, NY (US)

( * ) Notice: Subject to any disclaimer, the term of this patent is extended or adjusted under 35 U.S.C. 154(b) by 95 days.

(21) Appl. No.: 13/206,054

(22) Filed: Aug. 9, 2011

(65) Prior Publication Data

US 2012/0083813 A1 Apr. 5, 2012

Related U.S. Application Data (60) Provisional application No. 61/388,524, filed on Sep. 30, 2010.

(51) Int. Cl.
*A61B 17/32* (2006.01)
*A61B 17/04* (2006.01)

(52) U.S. Cl.
CPC . *A61B 17/320036* (2013.01); *A61B 2017/0496* (2013.01); *A61B 2017/320052* (2013.01); *A61B 17/0401* (2013.01); *A61B 2017/0417* (2013.01)
USPC .......................................................... 606/167

(58) Field of Classification Search
USPC ................................. 606/167, 170; 600/104
See application file for complete search history.

(56) References Cited

U.S. PATENT DOCUMENTS

| | | | |
|---|---|---|---|
| 184,804 A | 11/1876 | Stohlmann | |
| 1,967,888 A | 7/1934 | Kearsley | |
| 2,759,261 A | 8/1956 | Setecka | |
| 3,494,490 A | 2/1970 | Shell | |
| 3,650,274 A | 3/1972 | Edwards et al. | |
| 4,425,706 A | 1/1984 | Southworth et al. | |
| 4,499,898 A | 2/1985 | Knepshield et al. | |
| 4,538,611 A | 9/1985 | Kelman | |
| 4,617,713 A | 10/1986 | Pomerenke | |
| 4,646,722 A | 3/1987 | Silverstein et al. | |
| 4,672,734 A | 6/1987 | Kawada et al. | |
| 4,773,421 A | 9/1988 | Davis | |
| 4,962,766 A | 10/1990 | Herzon | |
| 5,273,024 A | 12/1993 | Menon et al. | |
| 5,306,284 A | 4/1994 | Agee et al. | |
| 5,323,765 A | 6/1994 | Brown | |
| 5,334,214 A | 8/1994 | Putnam | |
| 5,366,465 A | 11/1994 | Mirza | |
| 5,423,804 A | 6/1995 | Kulick | |
| 5,425,355 A | 6/1995 | Kulick | |
| 5,443,475 A | 8/1995 | Auerbach et al. | |
| 5,458,611 A | 10/1995 | Resnick et al. | |
| 5,549,623 A | 8/1996 | Sharpe et al. | |
| 5,569,283 A | 10/1996 | Green et al. | |
| 5,578,051 A | 11/1996 | Mirza | |
| RE35,523 E | 6/1997 | Berger | |
| 5,685,853 A | 11/1997 | Bonnet | |
| 5,735,865 A | 4/1998 | Schaumann et al. | |
| 5,769,865 A | 6/1998 | Kermode et al. | |
| 5,928,259 A | 7/1999 | Tovey | |
| 5,968,061 A | 10/1999 | Mirza | |

(Continued)

*Primary Examiner* — Katherine M Shi
(74) *Attorney, Agent, or Firm* — Shoemaker and Mattare (57) ABSTRACT

A sling blade apparatus allows percutaneous transaction of fascia or ligaments and in particular for use in transaction of the human transverse carpal ligament. A flexible sling guide is deployed percutaneously beneath the transverse carpal ligament and when drawn taut interfaces intimately with the transverse carpal ligament. The sling in turn serves as a guide along which cutting instruments can be passed to transect the ligament while simultaneously serving as a protective shield for the adjacent median nerve.

6 Claims, 11 Drawing Sheets

(56) References Cited

U.S. PATENT DOCUMENTS

| | | |
|---|---|---|
| 5,968,076 A | 10/1999 | Granger et al. |
| 6,120,525 A | 9/2000 | Westcott |
| 6,312,392 B1 | 11/2001 | Herzon |
| 6,346,106 B1 | 2/2002 | Jako |
| 7,010,352 B2 | 3/2006 | Hogan |
| 7,177,677 B2 | 2/2007 | Kaula et al. |
| 7,959,577 B2 | 6/2011 | Schmitz et al. |
| 2002/0010483 A1 | 1/2002 | Follmer et al. |
| 2004/0054378 A1 | 3/2004 | Yang |
| 2004/0098005 A1 | 5/2004 | Mirza et al. |
| 2004/0181246 A1* | 9/2004 | Heppler ............ 606/167 |
| 2004/0267243 A1 | 12/2004 | Klotz et al. |
| 2005/0070818 A1 | 3/2005 | Mueller |
| 2006/0184187 A1 | 8/2006 | Surti |
| 2007/0123889 A1 | 5/2007 | Malandain et al. |
| 2008/0306498 A1* | 12/2008 | Thatcher et al. ....... 606/159 |
| 2011/0087255 A1 | 4/2011 | McCormack et al. |
| 2012/0016398 A1* | 1/2012 | Strickland ............ 606/170 |

\* cited by examiner

SLING BLADE TRANSECTION OF THE TRANSVERSE CARPAL LIGAMENT

This application claims benefit of provisional patent application 61/388,524, filed Sep. 30, 2010.

BACKGROUND OF THE INVENTION

This invention relates to surgery and more particularly to percutaneous or endoscopic transection of the transverse carpal ligament.

First described in 1933, carpal tunnel release surgery is now considered the most frequently performed operation in the United States. Although carpal tunnel syndrome can be caused by a variety of clinical disorders (hypothyroidism, diabetes, pregnancy etc.), occupational injury or repetitive strain syndrome is now the most frequent association. Indeed, carpal tunnel syndrome is second only to back injuries as the most common reason for employee absenteeism. With repetitive use of the hand, the transverse carpal ligament is thought to hypertrophy thereby compressing the median nerve running beneath it causing the compression neuropathy known as carpal tunnel syndrome.

The carpal tunnel is formed dorsally by the proximal row of carpal bones. Ventrally, the broad ligament known as the transverse carpal ligament extends from the hook of the hamate bone medially to the trapezium bone laterally to form the roof or ventral boundary of the carpal tunnel. Within the tunnel pass the flexor tendons of the hand, the median nerve and associated synovial tissues associated with the flexor tendons.

While a variety of temporizing measures can be used to treat the condition (splinting, anti-inflammatory medication, steroid injection), only surgery is considered curative. Because surgery for this condition enjoys a very high success rate with low morbidity, it is frequently chosen as the definitive treatment option.

The surgical treatment of this condition can be broadly divided into two types: open versus minimally invasive (endoscopic or percutaneous).

With the open procedure, the skin lying over the carpal tunnel is incised and the transverse carpal ligament is then transected under direct vision. The skin is then reapproximated with sutures.

In the endoscopic version, small portals are made in the skin and the transverse carpal ligament is transected endoscopically or through small portals without major disruption of the overlying skin and subcutaneous tissues. In the percutaneous method the ligament is incised using small skin portals similar to the endoscopic method but does not need the use of an expensive endoscope to achieve the same result. Because the majority of pain receptors are located in the skin, limiting surgical trauma to the ligament results in significantly less pain attributable to the procedure and a shorter convalescent period.

Since endoscopic or percutaneous procedures involve smaller skin incisions as compared to the open procedures, they are favored by many surgeons in the treatment of this condition. Present endoscopic procedures require passing an endoscope and associated cutting instruments through the carpal tunnel to facilitate the endoscopic operation. In severe forms of carpal tunnel syndrome, the hypertrophied transverse carpal ligament renders the carpal tunnel quite narrow. Indeed, this is the pathologic process by which the median nerve becomes compressed. When the carpal tunnel is narrow, it becomes difficult and sometimes impossible to pass all of the necessary equipment needed to perform the release surgery. This occurs because the endoscope and associated instruments have a fixed diameter which the pathologically narrow carpal tunnel may not be able to accommodate. For this reason, fully 15% to 20% of endoscopic procedures cannot be completed and must be converted to open procedures. In addition, even in successful endoscopic procedures, significant parathesia may be noted postoperatively because of damage to the median nerve that occurs when surgical endoscopes and instruments are passed through a pathologically narrow carpal tunnel.

Therefore, one object of this invention is to avoid the need for an endoscope in performing percutaneous carpal transverse ligament transection.

SUMMARY OF THE INVENTION

According to this invention, the transverse carpal ligament is transected either endoscopically, or percutaneously without an endoscope, utilizing instruments which present minimal cross-sectional area, thereby allowing surgery to be preformed even in extremely tight or narrowed carpal tunnels.

To do this, a flexible guide—in the simplest rendition, a wire, but in the preferred embodiment a flexible spatula—is passed through a proximal skin portal and is retrieved through a skin portal which is distal to the transverse carpal ligament.

Once the guide (wire(s) or spatula) has been received at the distal portal it is anchored and drawn taut so that it intimately contacts the adjacent ligament or fascia in a sling-like fashion.

The sling guide (wire(s) or spatula) then serves as a track along which a cutting blade or instrument can be pulled or pushed to transect the ligament. Sufficient tension is maintained on the sling guide to maintain intimate contact with the ligament and to ensure that the translating cutting apparatus is held against the ligament with sufficient force to ensure that the ligament is transected. In the spatula embodiment, the flat undersurface opposite to the cutting blade serves as a protective shield to the dorsal median nerve and attendant ligaments. In the wire or filament embodiment, the stabilizing wings of the cutting apparatus serve to shield the nerve and ligaments.

To maintain sufficient tautness of the wire or spatula guide embodiments, the distal end of the sling assembly (wire or spatula) is anchored at the distal port, and tensile force is applied proximally, or vice versa. Once the wire or spatula is deemed sufficiently taut, a cutting blade assembly is slid onto the sling assembly and the blade is then pulled or pushed along the sling assembly in order to transect the volar carpal ligament.

An additional wire or wires attached to the cutting assembly may be employed to allow a pulling force, or a flexible rod may be used to allow a pushing force. In either event the blade is passed along the sling guide (wire or spatula) thereby transecting the ligament.

Once the ligament has been transected, the sling-blade assembly can be removed from either the proximal or distal portal and the portals closed with a single suture.

The method described is simpler than present minimally invasive methods and can be done without (or with) adjunctive endoscopy. In addition, by varying the heights of the cutting blade on the blade assembly, partial depth transaction of the ligament may be performed to preserve some functional integrity of the transverse carpal ligament while still allowing enlargement of the carpal tunnel and decompression of the median nerve.

The cutting assembly which is manipulated along the sling guide includes a midline dorsal blade—resembling a shark's dorsal fin—attached perpendicular to a wing having slots, grooves, rails or tunnels which engage the sling assembly in a stable fashion allowing only for to and fro movement along the linear axis of the sling. By tautening the sling assembly, the wing of the blade assembly is held in intimate proximity to the undersurface of the ligament while the dorsal cutting blade transects the ligament as the blade is slid along the tautened sling.

Tautening of the sling assembly in turn can be achieved by pulling on the ends of the assembly, or alternatively, by anchoring one end at a skin portal and pulling on the other. This invention can be employed with or without an endoscope thereby providing an additional benefit of substantial cost containment in addition to affording a percutaneous method of transecting ligaments or fascia with the instruments presenting the smallest cross-sectional area yet achieved.

BRIEF DESCRIPTION OF THE DRAWINGS

In the accompanying drawings,

FIGS. 13a-13d show a sequence of tip removal for a three-wire version of the invention;

FIGS. 14a-14d show a sequence of tip removal for the three-wire version;

DESCRIPTION OF THE PREFERRED EMBODIMENT

Figures 1, 2, 3, 4:
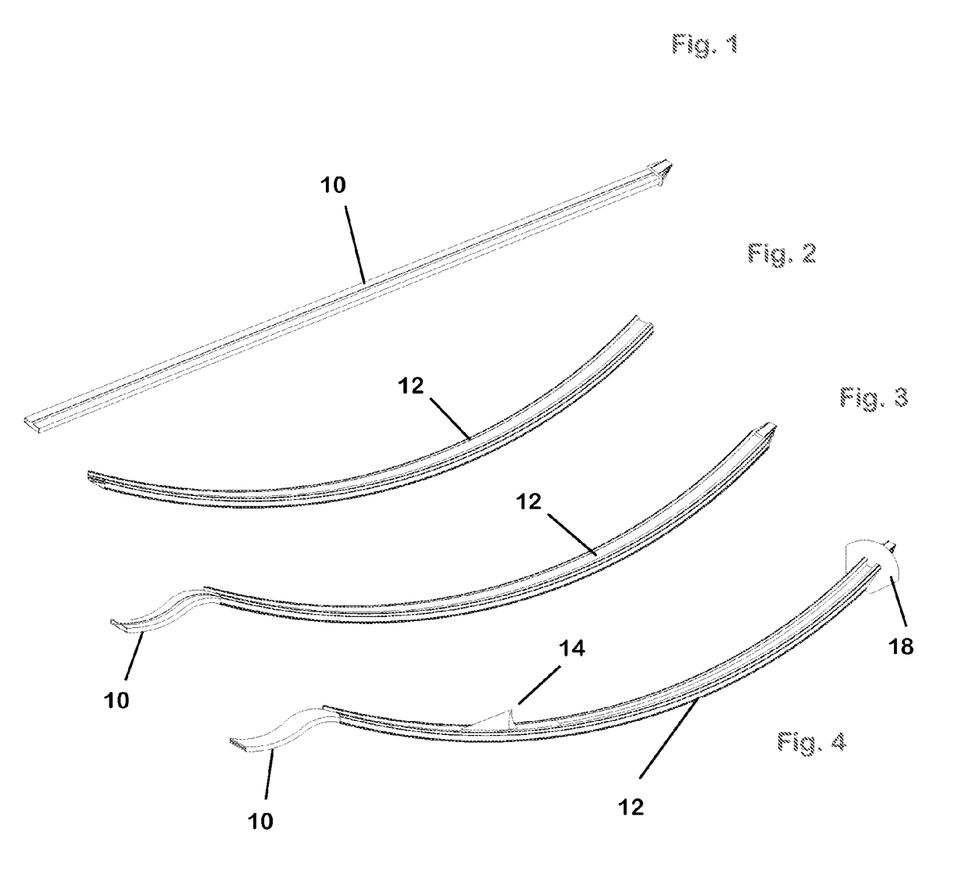
FIG. 1 is a perspective view of a channel for the spatula version of a sling blade device embodying the invention.
FIG. 2 is a perspective view of a curved channel embodying the spatula version.
FIG. 3 is a view like FIG. 2, showing a flexible guide inserted in the channel of the spatula version.
FIG. 4 is a view like FIG. 3, showing a cutting blade in the channel of the spatula version and an anchor on the distal end.

FIGS. 1-4 shows the components of a pass through tool. FIG. 1 illustrates a flexible knife guide tape 10 or spatula design. The spatula has a substantially ski-like shape to the advancing end so that it may serve as a soft tissue dissector and separate tissue planes with minimal trauma. FIG. 2 shows an arcuate rigid insertion guide 12 for the flexible knife guide tape, and FIG. 3 shows the guide loaded with the tape. FIG. 4 shows the guide with a push tape knife 14 inserted.

Figures 5A, 5B, 5C:
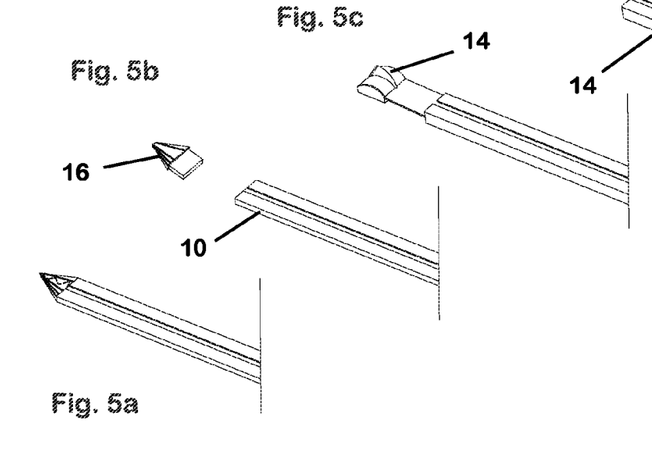
FIGS. 5a-5f show a sequence of steps for using the spatula version of the invention.
Figures 5D, 5E, 5F:
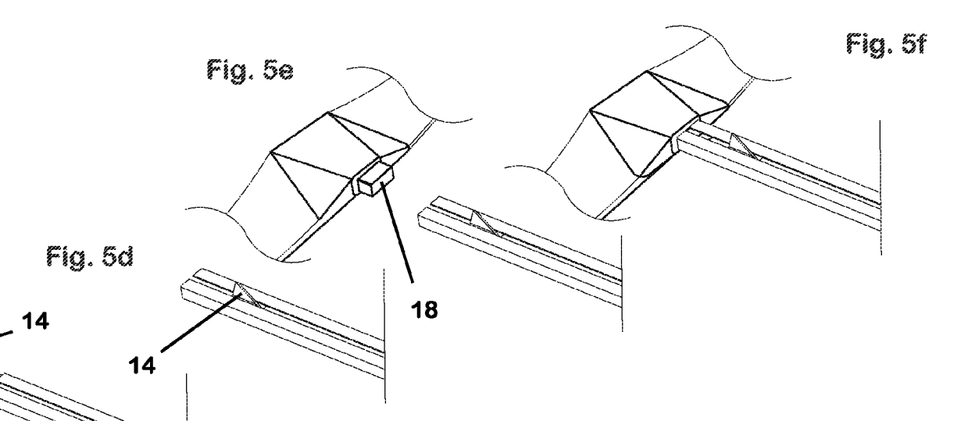

FIG. 5a shows the pass through tool 10 in its initial configuration. The removable tip 16 enables the surgeon to push the tool through an incision in the skin on one side of the carpal ligament, and underneath the ligament, and anchor it at the distal end. The curvature of the pass through tool causes it to surface on the hand side of the ligament, whereafter the tip may be removed as shown in FIG. 5b. Then a push tape with a cutting knife 14 attached is pushed back through the tool. The free end of the tape is grasped and the knife is pulled just into the guide, FIG. 5c. Now the distal end of the guide is secured, if desired, to an anchor 18 (FIGS. 5d,e) such as a fitting on a wrist band worn by the patient. Once the distal end is anchored, tension is applied on the proximal end of the guide to keep it against the bottom of the ligament.

Figure 6A:
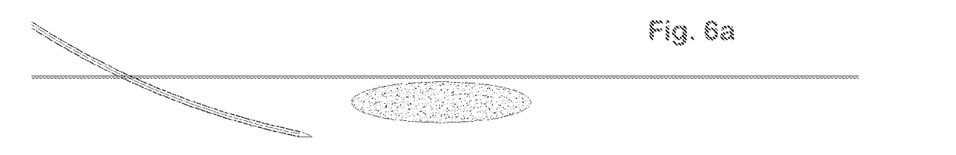
FIGS. 6a-6f show a sequence, viewed along the axis of the ligament, of the curved wire version being inserted percutaneously beneath the ligament.
Figure 6B:
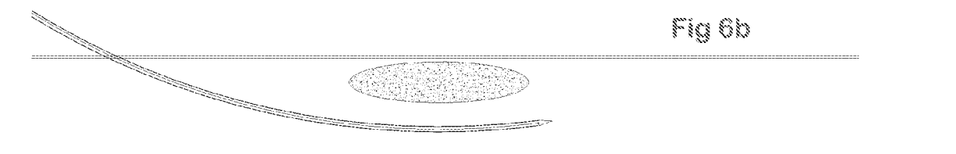
Figure 6C:
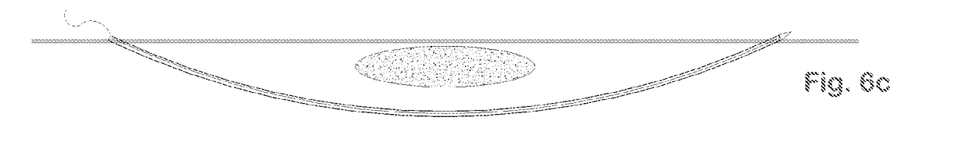
Figure 6D:
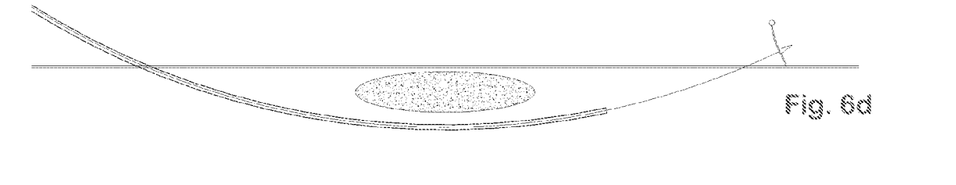
Figure 6E:
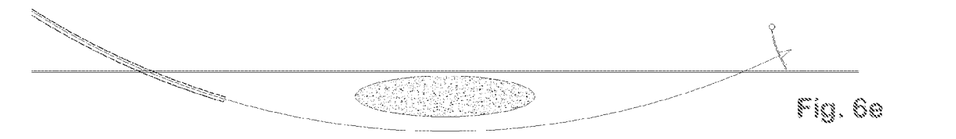
Figure 6F:
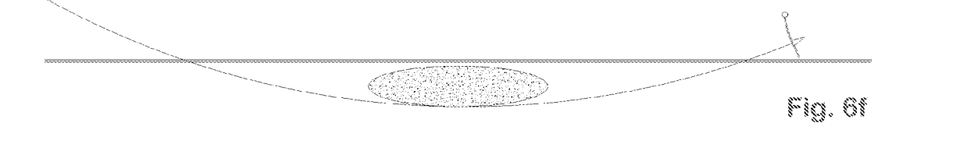

FIGS. 6a-6f illustrate the process in sectional views of the carpal ligament. FIGS. 6a and 6b show a curved guide wire or tape assembly being passed beneath the ligament. FIG. 6c shows the distal end of the curved guide wire assembly at the skin exit site. FIG. 6d shows the wire guide being anchored distally at the skin exit site, and the curved guide being removed. FIG. 6e shows the wire guide beneath the ligament and the curved guide almost exiting the proximal insertion site. FIG. 6f shows the wire guide being drawn taut against the undersurface of the ligament FIGS. 7-10 show a variation of the invention in which the knife guide is wire 10' or a pair of wires 10", rather than a tape or spatula channel. As with the previous embodiment, the wires are passed beneath the carpal ligament with a pass through tool having a removable tip 16'. In this case, the tip is secured to the distal ends of the guide wires. FIGS. 7a to 7d show the passing operation.

Figures 7A, 7B, 7C, 7D:
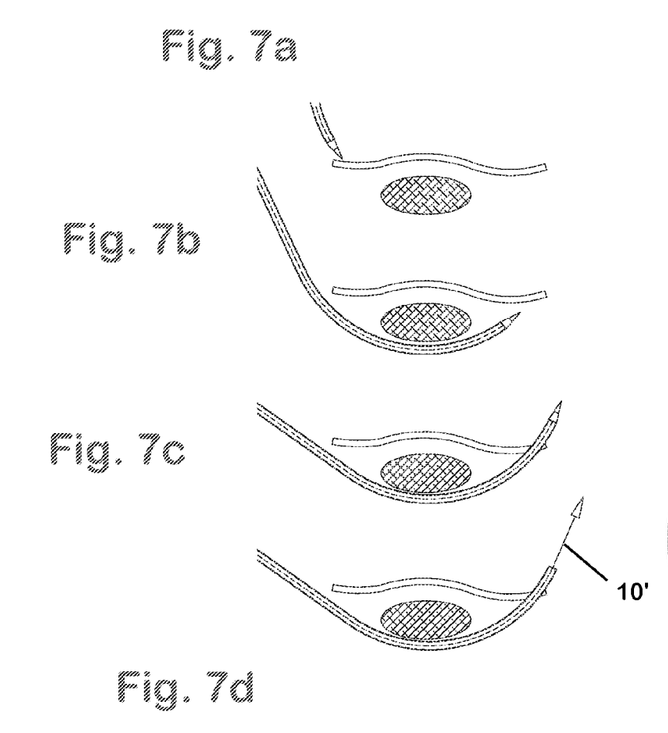
FIGS. 7a-7d depict a spatula or tape guide inserted beneath the ligament, similar to FIG. 6.
Figures 8A, 8B, 8C:
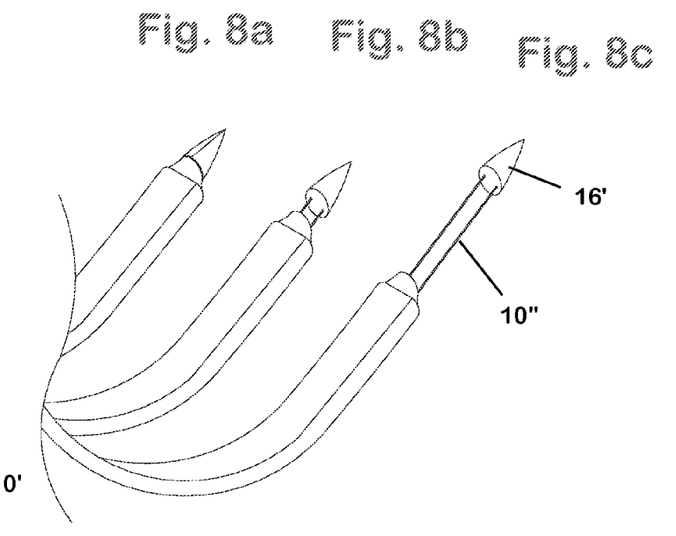
FIGS. 8a-8c show a tip removal sequence for a two-wire version of the invention.
Figures 9A, 9B:
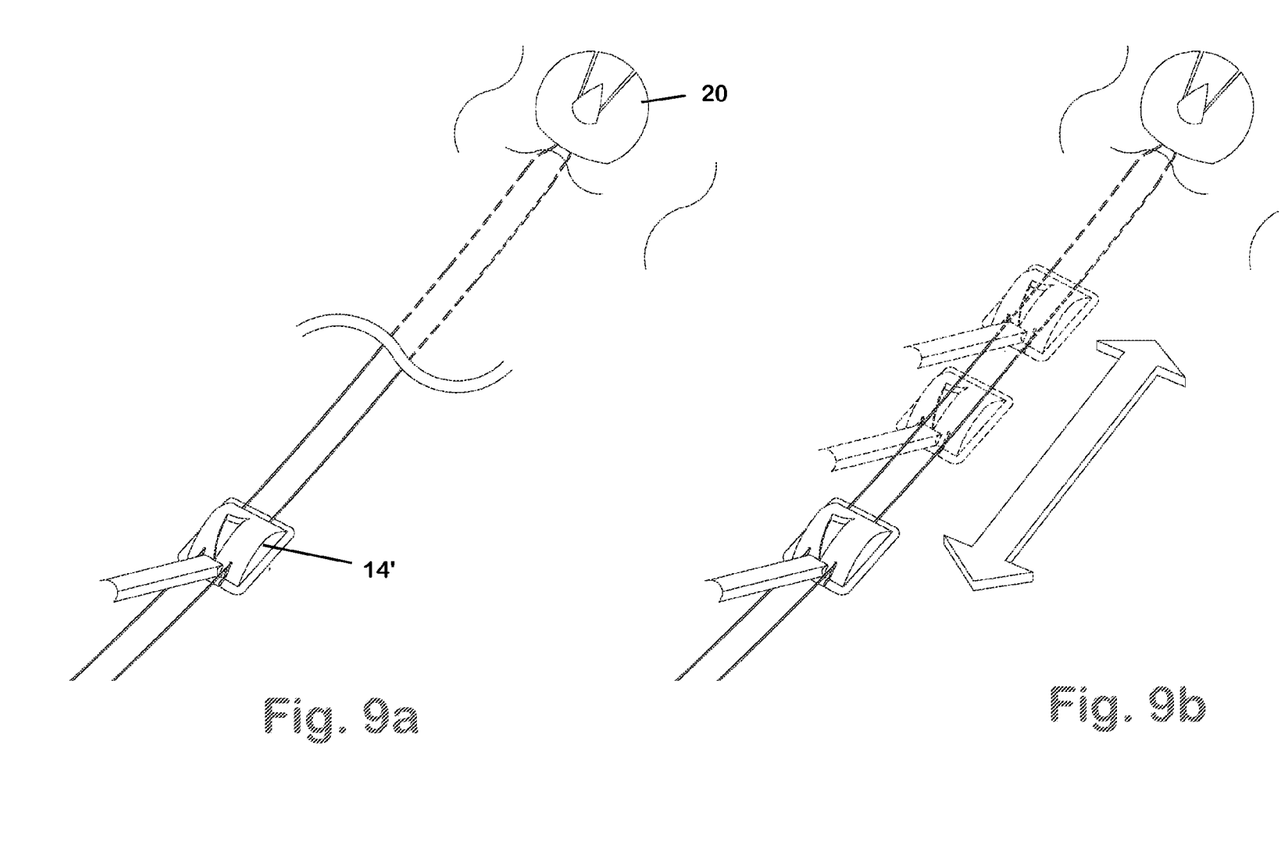
FIGS. 9a and 9b show steps of lacing the two-wire guide through the knife assembly as well as an anchor holding the distal tip at the skin surface.

FIGS. 8a to 8c show that, once the position of FIG. 7c is reached, the tip having emerged from the wrist, the tip may be pulled out of the pass through tool to expose a length of the wires.

The wires may then be seated in a pair of slots in an anchoring disk 20 (FIG. 9a) that rests on the skin surface when proximal tension is applied to the wires. In this case, the cutting knife is designed to cut when moving in the distal direction. The knife body 14' has two holes or slots 38, best seen in FIG. 18c, in which the respective wires are seated. Tension is maintained on the wires as the knife is pushed (or pulled) along them, cutting the ligament above.

Figures 10A, 10B:
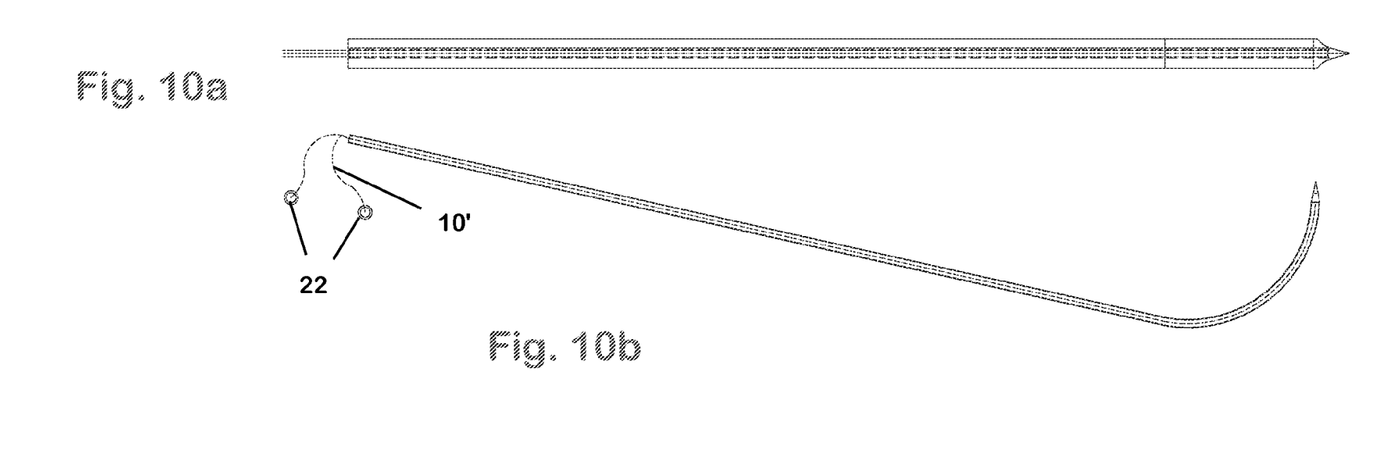
FIGS. 10a and 10b are top plan and side elevational views of the spatula or tape guide.

FIGS. 10 and 10b show the passing tool in two views, the latter showing beads 22 secured to the proximal ends of the wires. The beads are pulled to tighten the wires beneath the ligament.

Figures 11A, 11B, 11C, 12A, 12B:
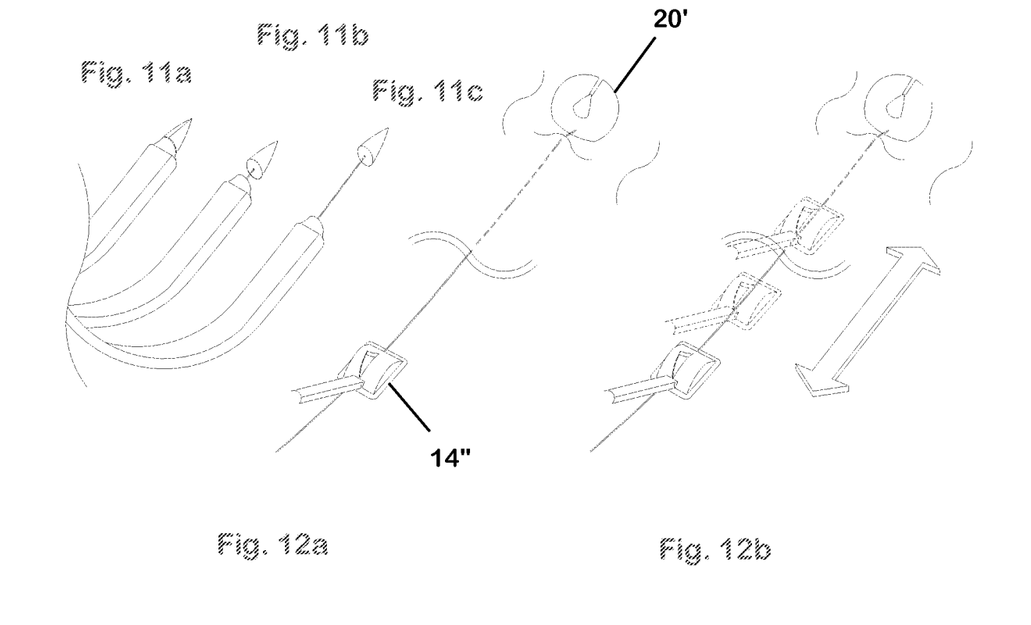
FIGS. 11a-11c show a sequence of tip removal for the single wire version.
FIGS. 12a and 12b show steps of lacing the single wire guide through the knife as well as the knife assembly translating along the wire guide beneath the ligament.

FIGS. 11 and 12 correspond to FIGS. 8 and 9, the only difference being that there is a single guide wire, instead of two. The anchoring disk 20' (FIG. 12a) and knife body 14" (FIG. 17c) are modified to receive a single wire.

Figure 13A:
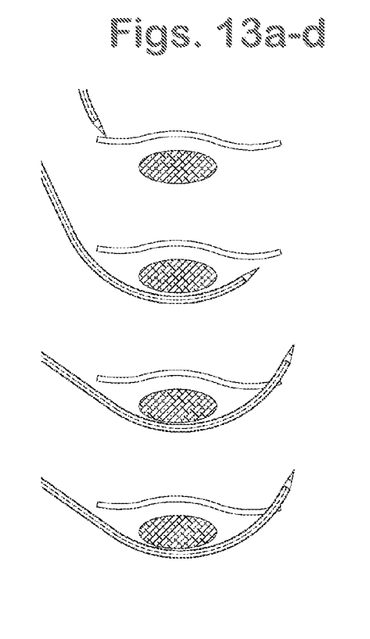
Figure 14A:
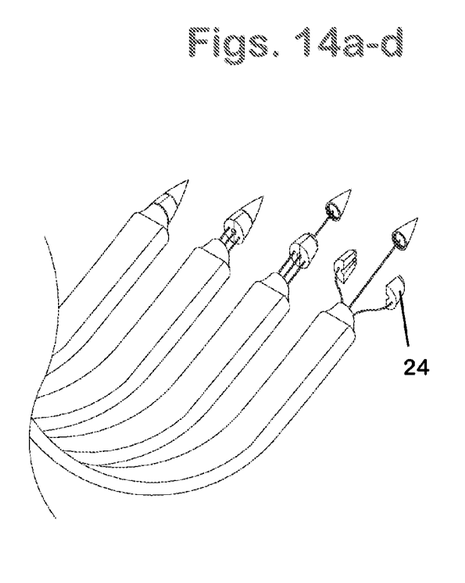
Figures 15A, 15B:
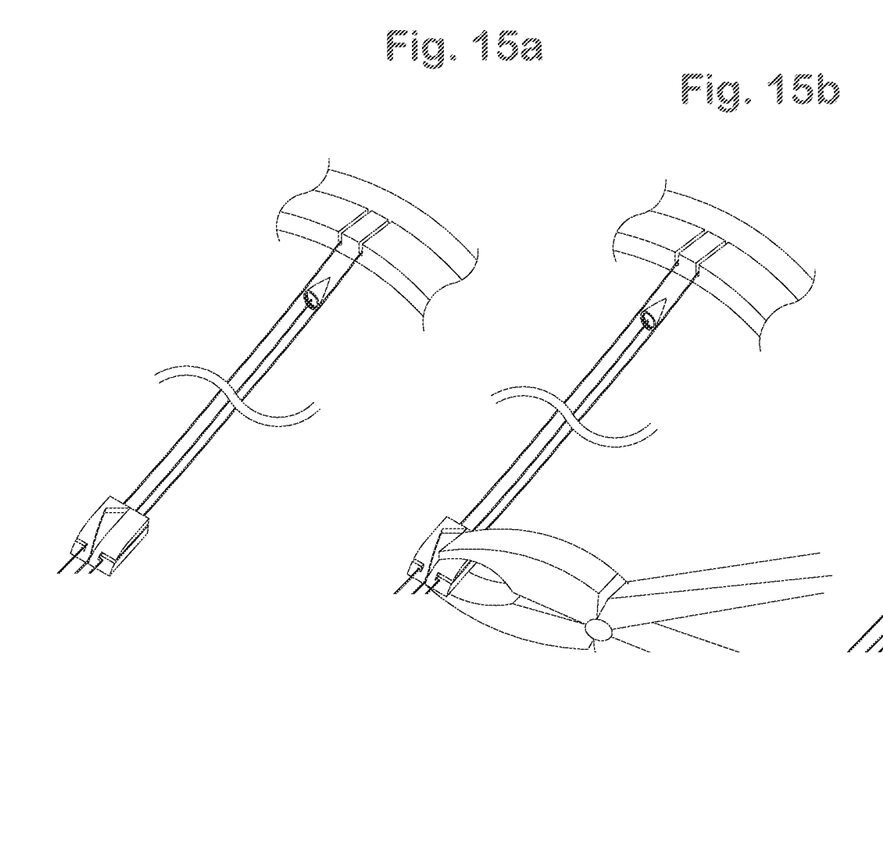
FIGS. 15a-15c shows steps of lacing the three-wire guide through the knife.
Figure 15C:
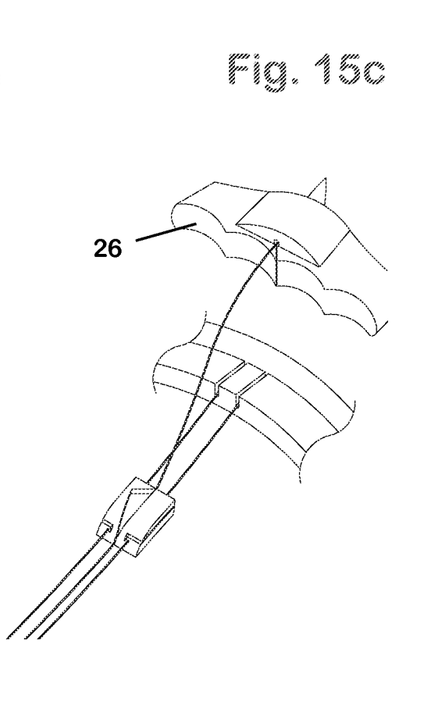

FIGS. 13-15 show a further variation in which there are three wires. This version is very similar to the two-wire version, except for the addition of a third wire. The outer wires serve as guides as previously described, and the knife moves along those wires while they are help in tension. The third wire is crimped to the knife body, and is used to pull the knife under the ligament. The distal end of the third wire is permanently secured to the removable tip of the pass through tool. The other two wires are secured to shells 24 which sandwich the third wire and support the tip during the passing phase. Once the tip emerges from the wrist, the shells can be separated (FIG. 14d) and a pull handle 26 (FIG. 15c) may be applied for the surgeon to grasp. As in the prior embodiments, the two guide wires are latched to a wrist strap at the exit incision site, so that they may be maintained in tension during the procedure.

Figure 16:
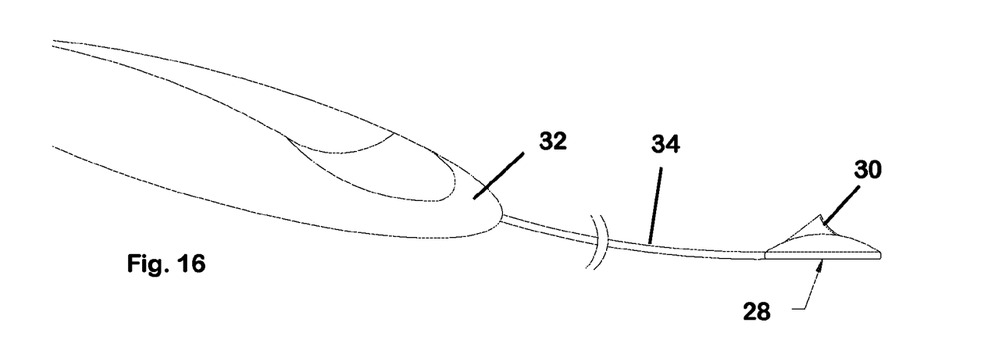
FIG. 16 is a side elevation of the knife, including its handle, using a flexible rod assembly.
Figures 17A, 17B:
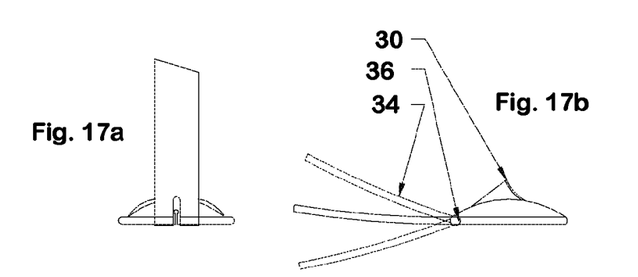
FIGS. 17a-17d are, respectively, rear, side, front and side elevations of the knife head in the single-wire version.
Figure 17C:
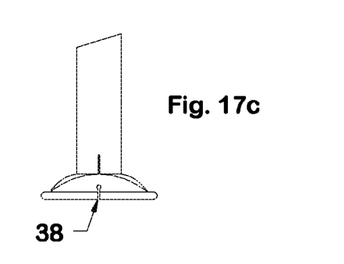
Figure 17D:
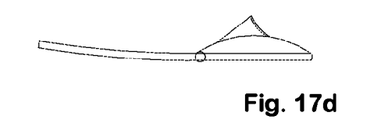
Figures 18A, 18B:
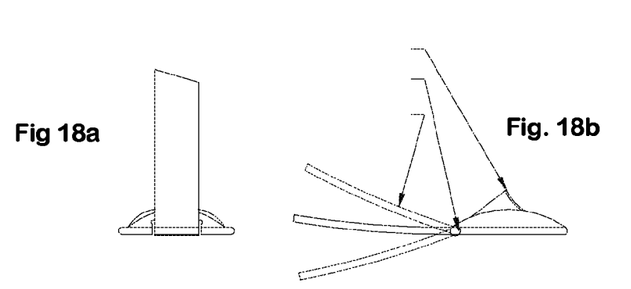
FIGS. 18a-18d are corresponding views for the two-wire version.
Figure 18C:
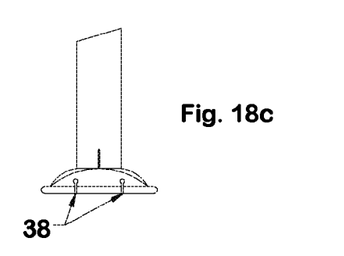
Figure 18D:
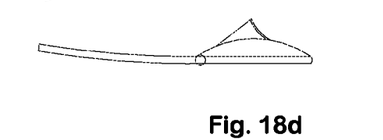
Figure 19A:
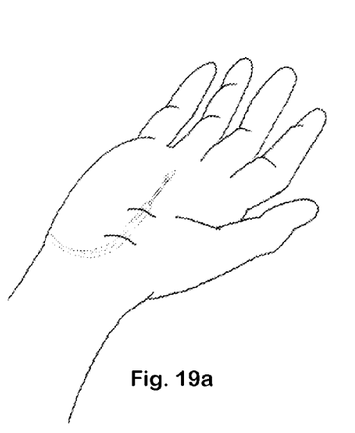
FIGS. 19a-19f show the sequence of steps on a hand.
Figure 19B:
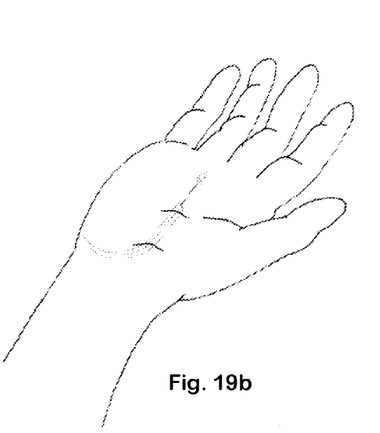
Figure 19C:
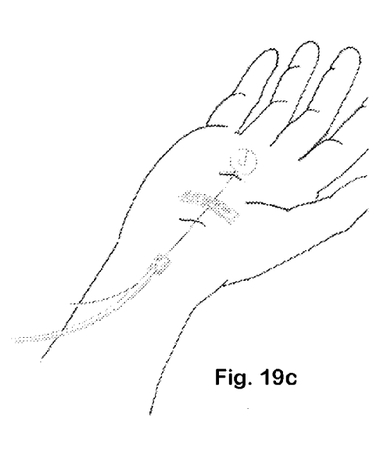
Figure 19D:
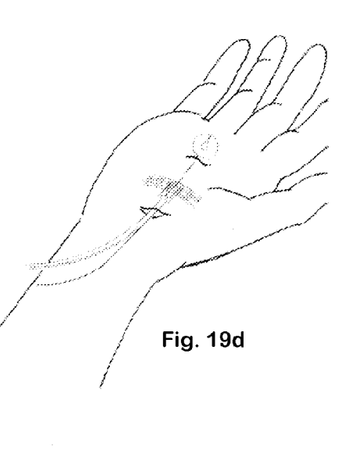
Figure 19E:
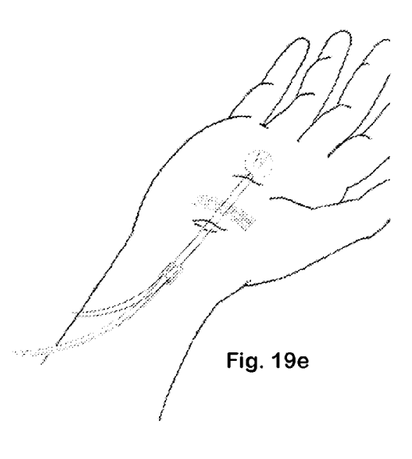
Figure 19F:
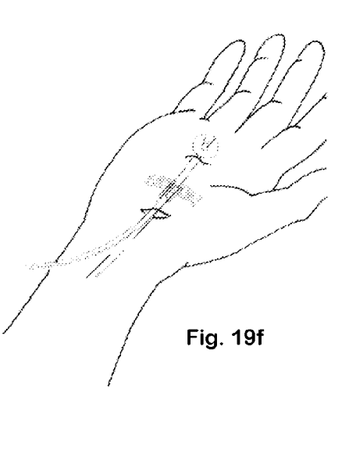

FIG. 16 shows a knife having a body 28 supporting a blade 30 extending upward, a handle 32, and a flexible push rod 34 extending from the handle for pushing the head in the cutting direction. FIGS. 17 and 18 show (for one- and two-wire versions, respectively) details of the head and of a pivot connection 36 between the distal end of the spatula and the head. The pivot allows the head to follow the direction of the guide wires during the transection.

The sequence of steps of a carpal tunnel procedure being performed on a patient's wrist are shown in FIGS. 19a-19f.

In the above descriptions, reference to "wire" should be understood to include polymeric filaments, and not to connote exclusively elements made from metal. Similarly, in the claims below, "wire" means metal wire or polymeric filament.

The foregoing are presently preferred embodiments of this invention. Variations are possible in which, for example, the knife body may pass around, over or through the guide. The important criteria are that the guide passes beneath the carpal ligament, and the knife body follows the guide as the knife is pushed or pulled along the guide. Furthermore, while this invention was designed for carpal ligament transection, it is, with suitable modifications, suitable for other procedures.

Since the invention is subject to modifications and variations, it is intended that the foregoing description and the accompanying drawings shall be interpreted as only illustrative of the invention defined by the following claims.

I claim:

1. An apparatus for transecting a fascia or a ligament percutaneously, said apparatus comprising:

a flexible guide comprising a spatula having a flat surface and sufficient tensile strength such that the flexible guide can be drawn taut beneath the fascia or ligament, and a cutting element having a blade for partially or fully transecting the fascia or ligament, said cutting element comprising a flat base slidably supported by the flat surface of the guide, and a cutting blade extending perpendicularly from said flat base, through a slot extending lengthwise of the guide, wherein the spatula has a detachable distal tip, said distal tip having wires or strings secured to said distal tip, such that said distal tip serves as an anchor at a distal skin portal thereby permitting the wires or strings to be drawn taut when tensile force is applied to them by pulling on the distal tip.

2. An apparatus according to claim 1, wherein the spatula has sufficient stiffness to be passed percutaneously beneath the fascia or ligament but retains sufficient flexibility or pliability that it can serve as a sling beneath the ligament when drawn taut.

3. An apparatus according to claim 1, wherein the spatula has a substantially ski-like shape to the advancing end so that it may serve as a soft tissue dissector and separate tissue planes with minimal trauma.

4. An apparatus according to claim 1, wherein the spatula may be detached from said wires or strings and then removed, whereafter the wires or strings then may serve as the sole guide for the cutting element.

5. An apparatus according to claim 1, wherein the ligament is a carpal ligament.

6. An apparatus according to claim 4, wherein one of said wires or strings is secured to the cutting element, whereby that wire or string may be used to pull the cutting element along the other wires or strings.

* * * * *